US005224470A

United States Patent [19]

Schnepp-Pesch et al.

[11] Patent Number: 5,224,470

[45] Date of Patent: Jul. 6, 1993

[54] APPARATUS FOR BIOPSY SAMPLING WITH NEEDLE AND STYLET MOVEABLE IN OPPOSITE DIRECTIONS

[75] Inventors: Wolfram Schnepp-Pesch, Ettlingen; Josef Lindenberg, Karlsruhe, both of Fed. Rep. of Germany

[73] Assignee: Angiomed AG, Karlsruhne, Fed. Rep. of Germany

[21] Appl. No.: 647,756

[22] Filed: Jan. 30, 1991

[30] Foreign Application Priority Data

Feb. 28, 1990 [DE] Fed. Rep. of Germany ....... 4006175

[51] Int. Cl.[5] ............................................ A61B 10/00

[52] U.S. Cl. .................................. 128/753; 128/754; 606/170

[58] Field of Search ............... 128/749, 750, 751, 752, 128/753, 754, 755, 760, 763, 765, 770; 606/167, 170, 168, 172, 181, 182, 184, 186; 604/156, 157, 134, 135, 902

[56] References Cited

U.S. PATENT DOCUMENTS

| | | | |
|---|---|---|---|
| 4,314,565 | 2/1982 | Lee | 128/753 |
| 4,600,014 | 7/1986 | Beraha | 128/754 |
| 4,699,154 | 10/1987 | Lindgren | 128/754 |
| 4,766,907 | 8/1988 | de Groot et al. | 128/754 |
| 4,817,631 | 4/1989 | Schnepp-Pesch et al. | 128/753 |
| 4,944,308 | 7/1990 | Akerfeldt | 128/751 |
| 4,958,625 | 9/1990 | Bates et al. | 128/754 |
| 5,036,860 | 8/1991 | Leigh et al. | 128/754 |

FOREIGN PATENT DOCUMENTS 9008507 1/1989 PCT Int'l Appl. .

*Primary Examiner*—Max Hindenburg
*Assistant Examiner*—Guy V. Tucker
*Attorney, Agent, or Firm*—Antonelli, Terry, Stout & Kraus

[57] ABSTRACT

An apparatus for sampling by means of biopsy is proposed, which has a hollow needle and a stylet guided therein, both of which being spring-loadable, the hollow needle being forwardly movable under spring tension and, prior to the advance of the hollow needle (32), the stylet (12) can be retracted under spring tension.

10 Claims, 1 Drawing Sheet

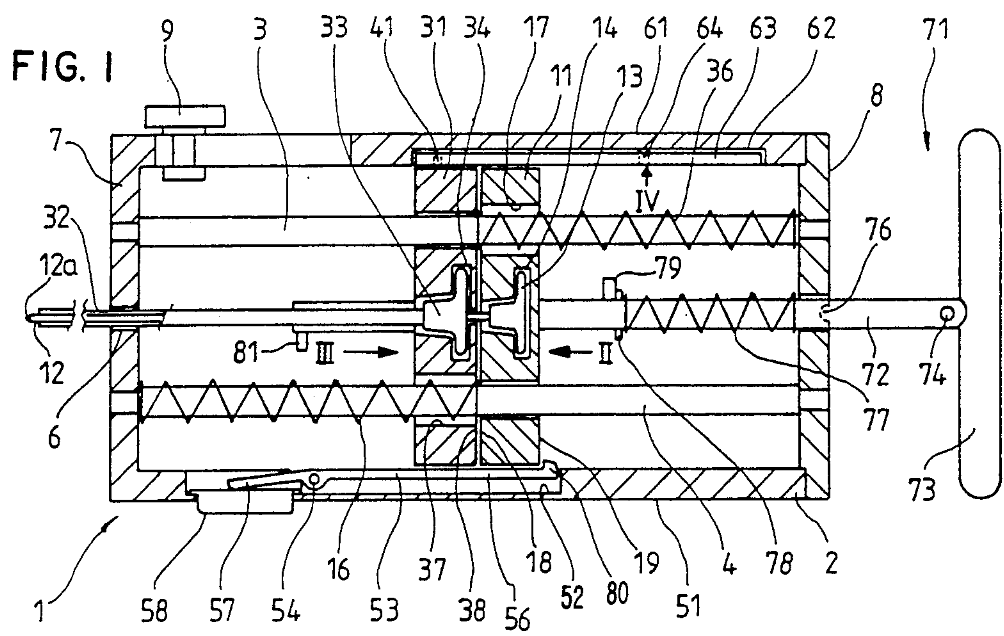
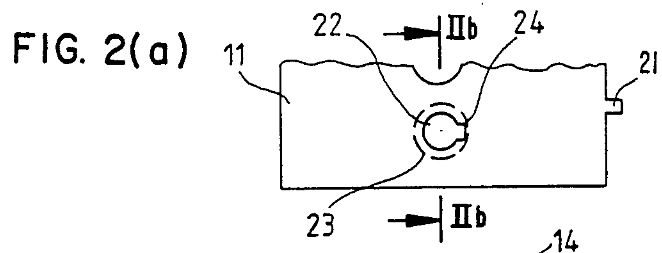
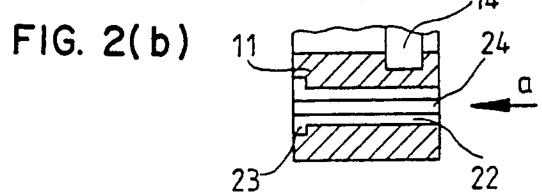
FIG. 3(a)
FIG. 3(b)
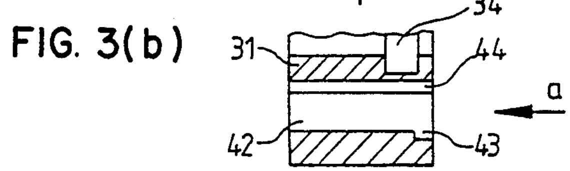

APPARATUS FOR BIOPSY SAMPLING WITH NEEDLE AND STYLET MOVEABLE IN OPPOSITE DIRECTIONS

FIELD OF THE INVENTION

The present invention relates to an apparatus for sampling or assay by biopsy, with the apparatus having a hollow needle and a stylet guided in the hollow needle, with both the hollow needle and stylet being spring loadable, and with the hollow needle being forwardly movable under a spring tension.

BACKGROUND OF THE INVENTION

An apparatus of the aforementioned type is proposed in, for example, EP-A-238 461, wherein the stylet, a so-called Tru-cut-Needle has a lateral receptacle. Under the action of a first spring, the Tru-cut-Needle is introduced into the biopsy area, so that the tissue is forced into the lateral recess. The hollow needle is then moved in the same direction over the recess, so that the tissue pressed into the latter is cut off and held by the Tru-cut-Needle, and the hollow needle and the stylet are moved jointly, with both needles being removed from the body so as to supply a tissue core for further investigation.

A similar but more complicated apparatus is proposed in, for example, WO83/03343.

EP-A-10 321 and EP-A-153 047 also disclose apparatuses wherein the stylet, having lateral indentations, is manually advanced and only the hollow needle is moved by spring action.

SUMMARY OF THE INVENTION

The aim underlying the present invention essentially resides in providing an improved sampling apparatus for a biopsy.

According to the present invention, an apparatus for biopsy sampling is provided with the apparatus including a hollow needle and a stylet guided in the hollow needle and with both the hollow needle and stylet being spring loaded. The hollow needle is forwardly movable under spring tension and the stylet can be retracted under spring tension prior to an advance of the hollow needle. Thus, the inventive apparatus uses a different procedure as compared with the prior art constructions. The stylet and then the hollow needle are not successively moved or fired over the stylet and, according to the invention, prior to the advance of the hollow needle, the stylet tip is retracted under the spring action into the hollow needle, with the hollow needle being subsequently advanced in a conventional manner under spring tension; however, unlike the prior art, the hollow needle cuts a completely cylindrical plug out of the tissue and, as a result of a vacuum resulting from a retracting of the stylet into the hollow needle, the tissue is drawn into the hollow needle and detached from the surrounding tissue.

As a result of the inventive sampling technique, it is possible to obtain the same tissue volume or a tissue part with the same cross section as in the prior art using a stylet and a hollow needle with much smaller cross sectional dimensions than in the prior art. Thus, the patient being examined is much less stressed, which is of particular importance in the case of sensitive body parts or organs.

Although, basically, the apparatus could have a Tru-cut-Needle, having a lateral recess which is not used in the inventive apparatus, according to a preferred embodiment of the invention, the stylet has a smooth, continuous cylindrical wall without any lateral recess. Only its tip is pointed, for example, in the form of trocar point.

Furthermore, the face of the hollow needle is also sharpened; however, the entire hollow needle face is preferably not tapered, as in the case with hollow needles used in conjunction with Tru-cut-Needles. Thus, the hollow needle face would be located in a vertical plane to its axis. The hollow needle wall can have lateral incisions from the face thereof and which, at least on one longitudinal edge, are also ground to form a sharp edge. As a result, a helical advance of the hollow needle and a helical cutting are possible. In such a construction, the hollow needle and, optionally, its grip or handle or holder secured in the same, is moved helically along and through an apparatus-fixed helical groove.

According to further embodiments of the present invention, the reception bodies or receptacles holding the needles can be tensioned or fixed against one another to counter the spring tensions acting thereon, and a fixing part with relatively reciprocally spaced fixing lugs may be provided for engaging the receptacles.

According to another embodiment of the present invention, the receptacles are provided on remote partitions thereof with undercuts for engagement with the lugs.

For securing the stylet in its active fixing position, a lever, operable from the outside, may have a nose for holding the stylet in the active fixing position. The hollow needle is secured in its active fixing position preferably through the lever holding the hollow needle in the position having, in an axially spaced manner from the fixing position of the stylet receptacle, a lever arm against which can be brought a receptacle lug for the stylet, so as to release the hollow needle from its active fixing position.

By virtue of the features of the biopsy apparatus of the present invention, an apparatus is provided which, as a result of the antithetic movement of the stylet and the hollow needle, that is, retraction of the stylet and subsequent advance of the hollow needle and, optionally accompanied by rotation thereof and, in each case, under spring tension, an efficient, reliable and rapid sampling is ensured, which minimizes stress for the patient. This is particularly helped by the fact that the stylet and hollow needle diameter can be made very small, but it is still possible to obtain an adequate sample volume or sample with an adequate cross section.

BRIEF DESCRIPTION OF THE DRAWINGS

The invention is described in greater detail hereinafter relative to non-limitative embodiments and the attached drawings, wherein:

FIG. 1 is a longitudinal cross-sectional schematic view of a biopsy sampling apparatus constructed in accordance with the present invention;

FIG. 2*a* is a partial view of the apparatus of FIG. 1 taken in the direction of the arrow II in FIG. 1;

FIG. 2*b* is a partial cross-sectional view taken along the lines II*b*–II*b* in FIG. 2*a;*

FIG. 3*a* is a plan view of another embodiment of a receptacle for a hollow needle similar to FIG. 2*a;*

FIG. 3*b* is a cross-sectional view similar to FIG. 2*b* of the receptacle for the hollow needle of FIG. 3*a* taken along the line 3*b*–3*b* in FIG. 3*a*; and FIG. 4 is a schematic view of a holding lever for the hollow needle taken in the direction of the arrow IV in FIG. 1.

DETAILED DESCRIPTION

A biopsy apparatus generally designated by the reference numeral 1, in accordance with the present invention, includes a casing 2 which can be closed by a cover (not shown). Two guide rods 3, 4 are disposed in the casing 2, with the guide rods 3, 4 being spaced and parallel to one another and extending in the longitudinal direction of the casing 2. Receptacles 11, 31 for the stylet 12 and hollow needle 32 are slidably arranged on the respective guide rods 3, 4, with a grip or handle 13 for the style 12 and a grip or handle 33 for the hollow needle 32 being accommodated in the respective receptacles 11, 31. The stylet 12 extends through the hollow needle 32 and, in a fully inserted position, a tip of the stylet 12 slightly projects out of the hollow needle 32. The grips 13, 33 of the stylet 12 and hollow needle 32 are received and held in reception recesses 14, 34 of the receptacle 11, 31. The hollow needle 32 extends with the stylet 12 received therein through a guide groove 6 in a front (proximal) partition 7 of the casing 2 and extends outwardly of the same.

Both receptacles 11, 31 are axially spring loaded so that they can advance under free spring action, with the receptacle 11 advancing to a rear (distal) casing partition 8 running parallel to the partition 7 and the receptacle 31 advancing to a stop 9 adjustable in a longitudinal or axial direction and fixable in a particular position.

For exerting the spring action, a compression spring 16, 36 is positioned around each of the guide rods 3, 4 and extends through a widened recess 37, 17 of the respective receptacles 31, 11 and engages on the facing sides 18, 38 of the receptacles, while respectively abutting on the front partition 7 for the spring 16 loading the receptacle 11 and on the rear partition 8 for the spring 36 loading the receptacle 31.

Thus, in the illustrated embodiment, the spring 16 surrounds the guide rod 4 and has a stationary abutment on the front partition 7, projects with its other end through the widened recess or opening 37 of the receptacle 31 and moves with its other end against the side face or wall 18 of the receptacle 11 facing the receptacle 31. The spring 36 surrounds the guide rod 3 and has a stationary abutment on the rear partition 8, extends through the widened recess or opening 17 of the receptacle 11 and presses the receptacle 31 by engagement on its side face or wall 38 in a direction towards the front partition 7 of the casing 2. In opposition to the spring tensions acting thereon, the receptacles 11, 31 are held in the illustrated position, in which their facing side faces or walls 18, 38 engage one another, with the disposition of the receptacles 11, 31 in the illustrated position being accomplished in the following manner.

A two-armed lever is held about a pivot pin 54 in a recess 52 on a longitudinal wall 51 of the casing 2. The two-armed lever 53 has a first lever arm 56 and a projecting nose 80 engageable behind the side face or wall 19 remote from the side face or wall 18 of the receptacle 11 and, in this manner, retains the receptacle 11 counter to the action of the spring 16. A button 58, mounted in the longitudinal wall 51 of the casing and projecting therefrom, engages the lever arm 57 remote from the lever arm 56 of the two-armed lever 53. If the button 58 is pressed into an interior of the casing 2, the button 58 presses the lever arm 57 and thereby pivots the two-armed lever 53 clockwise about the pivot pin 54, as viewed in FIG. 1, so that the projecting nose 80 of the lever 56 moves out of engagement with the side face or wall 19 of the receptacle 11 and releases the receptacle 11, so that together with the stylet held by the receptacle 11, the stylet 12 is moved under the spring action exerted thereon against the rear partition 8 of the casing 2 and, consequently, the tip 12*a* of the stylet 12 is retracted into the hollow needle 32.

On a side remote from the lever 53, the receptacle 31 is provided with a lug 41. A two-armed lever 63, pivotable by a pivot bearing 64, is also located in a recess 62 in the longitudinal wall of the casing 2, with the configuration of the two-armed lever 63 being more clearly illustrated in FIG. 4. At its front lever arm 67, the two-armed lever 63 has an undercut in the form of a groove 68, in which engages lug 41 of the receptacle 31, so that the receptacle is held in the locking position shown in FIG. 1 in opposition to the spring action pressing thereon. Under spring action, the lever 63 is forced into the position shown in FIG. 4 engaging the lug 41. The spring 69 is attached at one end to the swivel bearing 64 provided on the casing 2 and a free end of the spring 69 presses against a lever arm 66 of the lever 63.

A lug 21, corresponding to the lug 41, is provided on the side of the receptacle 11 facing the lever arm 63. If the receptacle 11 is released in the aforementioned manner from its locked position and moves under spring action against the partition 8, the lug 21 first engages the lever arm 66 and presses the lever arm 66 counter to the action of the spring 69, namely, in a downward direction or clockwise direction as viewed in the drawings.

Consequently, the lever arm 67 is raised with respect to the lug 41, so that the groove 68 releases the lug 41 and releases the receptacles 31. The receptacle 31 is then forced under spring action toward the front partition 7 until striking the stop 9. Thus, with the receptacle 31, the hollow needle 32 is advanced further into the tissue region of interest, cut a tissue plug therefrom and, under vacuum brought about by the hollow needle 32 as a result of the retraction of the stylet 12, the tissue plug is detached from the surrounding tissue and drawn into the hollow needle 32.

For the renewed fixing of the biopsy apparatus, a fixing part generally designated by the reference numeral 71 is provided, with the fixing part 71 including a rod 72 and a grip 73. The rod 72 extends longitudinally, i.e., parallel to the guide rods 3, 4, through the rear partition 8 into the casing 2 and through openings 22, 42 (FIGS. 2*a*, 3*a*) of the receptacles 11, 31. Outside the casing, the grip 73 is connected to the rod 72 and extends at right angles thereto. A lug 74 is provided on the rod 72 directly upstream of the grip 73, with the lug 74 being engageable in a corresponding recess of the rear partition 8, so as to maintain the grip 73 in an inoperative position permitting a biopsy sampling.

The fixing part 71 can be spring loaded. In this case, a compression spring 77 is arranged around the rod 72, with the compression spring 77 having a stationary abutment on the partition 8 and being held by an abutment 78 fixed to the rod 72 so as to press the fixing part 71 into the casing and the grip 73 against the partition 8.

Radial lugs 79, 78 are arranged in an axially spaced manner on the rod 72. On the partition remote from the receptacle 31, the receptacle 11 has an undercut 23 (FIG. 2*a*), on which the lug 79 can engage upon rotation of the rod by the grip 73 by approximately 90°, so that, by pressing the grip 73 and the rod 72 in the direction of the arrow a (FIGS. 2*b*, 3*b*) the receptacle 11 is pressed away from the rear partition 8 in the direction of the front partition 7 until the receptacle 11 slides along a bevel of the nose 80, with nose 80 and thereby the arm 56 being retracted. Upon the receptacle 11 passing over the bevel of the nose 80, the nose 80 engages behind the receptacle 11, so that the receptacle 11 is held by the nose 80 in the active or fixing position shown in FIG. 1. By further rotation, e.g. once again by 90°, the lug 81 can be brought into an undercut 43 (FIG. 3*b*) in the receptacle 31 and, by retraction of the grip 73, via the lug 41, the receptacle 31 can again be retracted into its active or fixing position until the groove 86 engages on the lug 41 of the receptacle 31 and, consequently, holds the receptacle 31 in the active or fixing position. Laterally of the openings 22, 42 (FIGS. 2*a*, 3*a*) for the rod 72, the receptacles 11, 31 have grooves 24 or 44 (FIGS. 2*b*, 3*b*) making it possible for the receptacles 11, 31 in the inoperative position of the fixing part (in which the lug 34 engages in the recess 76) to slide freely over the lugs 79, 81 and not be impeded in their movement under the action of the spring 16, 36 or not engaged on the fixing part 71.

Thus, the fixing process is performed in such a manner that the fixing part 71 is drawn out of the casing 2, with the lug 79 sliding through the groove 24. Subsequently, the fixing part 71 is rotated by 90°, so that the lug 79 comes to rest behind the undercut 43. The fixing part 71 is then pressed inward until the nose 80 of the lever 56 engages behind the receptacle 11 and holds the same. During this process, the lug 81 projects upwardly (i.e. out of the plane of the drawing). Therefore, the lug 81 can be moved through the groove 44 of the opening 42. A further 180° rotation brings the lug 41 behind the undercut 43 of the receptacle 41, which, by retraction, can also be brought into its fixing position held by the lever 63. A further 90° rotation and release of the fixing part 71 brings the fixing part 71, in the rotary position shown in FIG. 1, under the action of the spring 77 into its inoperative position, where the lug 34 engages in the recess 76. The biopsy sampling is then carried out in that first the hollow needle 32 and the stylet 12, with the tip 12*a* projecting slightly out of the hollow needle 32, are manually brought into the biopsy area of interest by manual advance of the biopsy apparatus 1. The biopsy sampling can then be carried out in the aforementioned manner starting by the operation of the push button 58 and then the bioptate can be removed from the body by retracting the complete biopsy apparatus 1.

We claim:

1. Apparatus for biopsy sampling, the apparatus comprising a hollow needle, a stylet guided in said hollow needle, a first means for spring loading said hollow needle comprising a first compressed spring, a second means or spring loading said stylet comprising a second compressed spring, said hollow needle being movable in a forward direction/upon the release of said first compressed spring and said stylet being movable in a rearward direction upon the release of said second compressed spring prior to the forward movement of the hollow needle, and a means for initiating said movement of the hollow needle in the forward direction upon the release of said first compressed spring in response to the rearward movement of the stylet.

2. Apparatus according to claim 1 wherein receptacle means are provided for respectively holding the stylet and the hollow needle in a selected fixed position in opposition to the spring forces.

3. Apparatus according to claim 2, further comprising a fixing means or enabling a selective positioning the stylet and the hollow needle, said fixing means including a rod and axially spaced lugs for in engagement with the respective receptacle means.

4. Apparatus according to claim 3, wherein the receptacle means are each provided with undercut portions for engagement with said lugs.

5. Apparatus for biopsy sampling, the apparatus comprising a hollow needle, a stylet guided in said hollow needle, means for spring loading said hollow needle and said stylet, said hollow needle being movable in a forward reaction upon the release of a spring, means for enabling a retraction of the stylet upon the release of a second spring prior to an advancement of the hollow needle, receptacle means for respectively holding the stylet and the hollow needle in a selected fixed position in opposition to the spring forces, a fixing means for enabling a selective positioning of the stylet and the hollow needle, said fixing means including a rod and axially spaced lugs for engagement with the respective receptacle means, bore means in the respective receptacle means for accommodating the rod of the fixing means, and wherein groove means are provided in the respective bore means for accommodating said lugs.

6. Apparatus according to one of claims 2 or 5, wherein a lever means including a nose portion cooperable with the receptacle means associated with the stylet is provided for maintaining the stylet in a fixed position.

7. Apparatus according to claim 6, wherein a further lever means for maintaining the hollow needle in a fixed position is provided, said further lever means including a lever arm cooperable with a lug of the receptacle associated with the stylet so as to enable a release of the hollow needle from the fixed position and thereby enable forward movement of the hollow needle.

8. Apparatus according to claim 7, further comprising a stop means adjustable int the axial longitudinal direction of the apparatus for limiting a movement of the receptacle means associated with the hollow needle in the forward direction.

9. Apparatus for biopsy sampling, the apparatus comprising a casing a hollow needle accommodated in the casing, a stylet axially movably guided in said hollow needle, said stylet having a smooth continuous cylindrical wall without lateral recesses, a tip portion of the stylet extends from a front end of the hollow needle when the stylet is disposed in an insertion position, a first spring engageable with the stylet for urging the stylet into a second position in which the tip of the stylet is retracted into the hollow needle, and a second spring engageable with the hollow needle and urging the hollow needle in a direction opposite to the first spring, and wherein the second spring urges the hollow needle into a second position which penetrates a tissue to be collected and cuts a core out of the tissue wherein said second spring urges said hollow needle into said second position in response to the first spring urging the stylet into said second position.

10. Apparatus for sampling by biopsy, the apparatus comprising a hollow needle and a stylet guided therein, a first and second compressed spring for respectively loading the hollow needle and the stylet, the hollow needle being movable forwards upon the release of the first compressed; wherein, prior to advance to the hollow needle, the stylet is retractable upon the release of the second compressed spring, said hollow needle moving forward in response to the retraction of the stylet, a fixing pat is provided including a rod and spaced lugs for engaging on receptacles for respectively holding the hollow needle and the stylet, and wherein the respective receptacles are provided with bores for allowing a passage of the rod of the fixing part, with grooves passing through the bores.

* * * * *